(12) United States Patent
Bernal-Mendez et al.

(10) Patent No.: US 8,637,322 B2
(45) Date of Patent: Jan. 28, 2014

(54) METHOD FOR LABELING OR TREATING A BIOLOGICAL SAMPLE CONTAINING BIOLOGICAL MOLECULES OF INTEREST, IN PARTICULAR NUCLEIC ACIDS

(75) Inventors: Eloy Bernal-Mendez, Saint Quentin Fallavier (FR); Ali Laayoun, Colombe (FR); Lionel Menou, Saint Genis Laval (FR)

(73) Assignee: Biomerieux, Marcy l'Etoile (FR)

( * ) Notice: Subject to any disclaimer, the term of this patent is extended or adjusted under 35 U.S.C. 154(b) by 408 days.

(21) Appl. No.: 11/919,668

(22) PCT Filed: May 31, 2006

(86) PCT No.: PCT/FR2006/001228
§ 371 (c)(1),
(2), (4) Date: Oct. 31, 2007

(87) PCT Pub. No.: WO2006/129010
PCT Pub. Date: Dec. 7, 2006

(65) Prior Publication Data
US 2009/0215188 A1 Aug. 27, 2009

(30) Foreign Application Priority Data
Jun. 1, 2005 (FR) .................... 05 51452

(51) Int. Cl.
*G01N 33/48* (2006.01)
*C07H 1/00* (2006.01)
(52) U.S. Cl.
USPC ............... 436/94; 436/43; 435/6.1; 435/91.2; 536/32; 536/25.32
(58) Field of Classification Search
USPC ............ 436/94, 43, 903; 536/25.32, 32; 435/6.1, 91.2
See application file for complete search history.

(56) References Cited

U.S. PATENT DOCUMENTS

| 4,507,466 A | 3/1985 | Tomalia et al. |
| 4,568,737 A | 2/1986 | Tomalia et al. |

(Continued)

FOREIGN PATENT DOCUMENTS

| DE | 39 10 151 A1 | 10/1990 |
| EP | 0 201 184 A2 | 12/1986 |

(Continued)

OTHER PUBLICATIONS

Kirschner, S. Inorganic Coordination Compounds in General Chemistry.(1958) 35:3: 139-141.*

(Continued)

*Primary Examiner* — Krishnan S Menon
*Assistant Examiner* — Rebecca M Fritchman
(74) *Attorney, Agent, or Firm* — Oliff & Berridge, PLC

(57) ABSTRACT

The present invention relates to a method for labeling biological molecules of interest contained in a biological sample, consisting in:
a) providing a reaction vessel,
b) immobilizing capture molecules, which are capable of binding a label of the biological molecules of interest, on a solid support of the vessel,
c) introducing the biological sample but also at least one label of the biological molecules of interest into said vessel and optionally any ingredient required for labeling or prelabeling the molecules of interest,
d) incubating the vessel content and immobilizing the label which is not reacted with the molecules of interest by binding to the capture molecules, and
e) using the labeled molecules of interest for subsequent steps.

A method for treating a biological sample is also disclosed. Said invention is preferably used in a manual or automated method for purifying nucleic acids.

14 Claims, 2 Drawing Sheets

(56) References Cited

U.S. PATENT DOCUMENTS

| | | | |
|---|---|---|---|
| 4,672,040 A | 6/1987 | Josephson | |
| 4,683,195 A | 7/1987 | Mullis et al. | |
| 4,683,202 A | 7/1987 | Mullis | |
| 4,800,159 A | 1/1989 | Mullis et al. | |
| 5,234,809 A | 8/1993 | Boom et al. | |
| 5,244,816 A * | 9/1993 | Subramanian | 436/545 |
| 5,328,824 A | 7/1994 | Ward et al. | |
| 5,399,491 A | 3/1995 | Kacian et al. | |
| 5,449,767 A | 9/1995 | Ward et al. | |
| 5,489,653 A | 2/1996 | Charles et al. | |
| 5,750,338 A | 5/1998 | Collins et al. | |
| 6,017,707 A | 1/2000 | Mandrand et al. | |
| 6,033,853 A | 3/2000 | Delair et al. | |
| 6,083,708 A | 7/2000 | Singh et al. | |
| 6,376,179 B1 | 4/2002 | Laayoun | |
| 6,414,136 B1 | 7/2002 | Spicer et al. | |
| 6,608,213 B1 * | 8/2003 | Sato et al. | 549/224 |
| 2002/0155496 A1 | 10/2002 | Charles et al. | |
| 2004/0110167 A1 * | 6/2004 | Gerdes et al. | 435/6 |

FOREIGN PATENT DOCUMENTS

| | | |
|---|---|---|
| EP | 0 302 175 A2 | 2/1989 |
| EP | 0 329 198 A2 | 8/1989 |
| EP | 0 063 879 B1 | 11/1989 |
| EP | 0 097 373 B1 | 10/1992 |
| EP | 0 561 722 A1 | 9/1993 |
| EP | 0 567 841 A2 | 11/1993 |
| EP | 0 569 272 A1 | 11/1993 |
| EP | 0 286 898 B1 | 4/1998 |
| EP | 0 669 991 B1 | 11/1999 |
| EP | 0 827 552 B1 | 1/2002 |
| FR | 2 607 507 A1 | 6/1988 |
| FR | 2 781 802 A1 | 2/2000 |
| FR | 2 868 071 A1 | 9/2005 |
| WO | WO 90/01069 A1 | 2/1990 |
| WO | WO 90/06995 A1 | 6/1990 |
| WO | WO 91/02818 A1 | 3/1991 |
| WO | WO 93/16094 A2 | 8/1993 |
| WO | WO 95/08000 A2 | 3/1995 |
| WO | WO 97/45202 A1 | 12/1997 |
| WO | WO 98/05766 A1 | 2/1998 |
| WO | WO 99/15621 A1 | 4/1999 |
| WO | WO 99/35500 A1 | 7/1999 |
| WO | WO 99/53304 A1 | 10/1999 |
| WO | WO 00/05338 A1 | 2/2000 |
| WO | WO 00/07982 | 2/2000 |
| WO | WO 00/40590 A2 | 7/2000 |
| WO | WO 00/60049 A1 | 10/2000 |
| WO | WO 01/44506 A1 | 6/2001 |
| WO | WO 01/44507 A1 | 6/2001 |
| WO | WO 01/92361 A1 | 12/2001 |
| WO | WO 02/090319 A1 | 11/2002 |

OTHER PUBLICATIONS

Jencks et al., "Reactivity of Nucleophilic Reagents toward Esters," *J. Amer. Chem. Soc*, 1960, vol. 82, p. 1778-1786.

O'Donnell et al., "Reporter Groups for the Analysis of Nucleic Acid Structure," *Bioorganic Chemistry: Nucleic Acids*, 1996, ed. Hecht S.M., Oxford University Press, p. 216-245.

Randolph et al., "Stability, specificity and fluorescence brightness of multiply-labeled fluorescent DNA probes," *Nucleic Acids Research*, 1997, vol. 25, No. 14, p. 2923-2929.

Chevalier et al., "Biotin and Digoxigenin as Labels for Light and Electron Microscopy in Situ Hybridization Probes: Where Do We Stand?" *The Journal of Histochemistry & Cytochemistry*, 1997, vol. 45, No. 4, p. 481-491.

Egholm et al., "Peptide Nucleic Acids (PNA). Oligonucleotide Analogues with an Achiral Peptide Backbone," *J. Am. Chem. Soc.*, 1992, vol. 114, p. 1895-1897.

Steininger et al., "Effectiveness of Reverse Transcription-PCR, Virus Isolation, and Enzyme-Linked Immunosorbent Assay for Diagnosis of Influenza A Virus Infection in Different Age Groups," *Journal of Clinical Microbiology*, 2002, vol. 40, No. 6, p. 2051-2056.

Troesch et al., "*Mycobacterium* Species Identification and Rifampin Resistance Testing with High-Density DNA Probe Arrays," *Journal of Clinical Microbiology*, 1999, vol. 37, No. 1, p. 49-55.

Laayoun et al., "Aryldiazomethanes for Universal Labeling of Nucleic Acids and Analysis on DNA Chips," *Bioconjugate Chemistry*, 2003, vol. 14, No. 6, p. 1298-1306.

Laayoun et al., "Universal Labeling Chemistry for Nucleic Acid Detection on DNA Chips," *Methods in Molecular Biology*, 2004, vol. 288, p. 241-250.

Kotera et al., "Pyrenyldiazomethane, a versatile reagent for nucleotide phosphate alkylation," *Bioorganic & Medicinal Chemistry Letters*, 2005, vol. 15, p. 705-708.

Bourget et al., "Biotin-phenyldiazomethane conjugates as labeling reagents at phosphate in mono and polynucleotides," *Bioorganic & Medicinal Chemistry*, 2005, vol. 13, p. 1453-1461.

\* cited by examiner

METHOD FOR LABELING OR TREATING A BIOLOGICAL SAMPLE CONTAINING BIOLOGICAL MOLECULES OF INTEREST, IN PARTICULAR NUCLEIC ACIDS

The present invention relates to a novel method for purifying a biological sample containing nucleic acids of interest, synthetic or natural ribonucleic acids (RNAs) or deoxyribonucleic acids (DNAs), which have been labeled.

The term "synthetic RNA or DNA" should be understood to mean RNA or DNA obtained by means of a technique developed by man, for example an amplification technique (PCR optionally followed by a transcription) or transcriptional amplification technique (TMA or NASBA). The term "natural RNA or DNA" should be understood to mean RNA or DNA obtained by extraction of a cell, for example messenger RNA, ribosomal RNA, transfer RNA or genomic DNA.

The prior art shows that many methods exist for labeling such nucleotides, oligonucleotides or nucleic acids. The oligonucleotides and the nucleic acids will all be subsequently referred to as polynucleotides. The labeling can be carried out either during synthesis, or by incorporation of at least one labeled nucleotide.

A first method consists in attaching the label to the base, irrespective of whether the latter is natural or modified. A second method proposed is attaching the label to the sugar, once again irrespective of whether it is natural or modified. A third method aims to bind the label to the phosphate.

Labeling on the base has in particular been used in the approach of labeling nucleic acids by incorporation of directly labeled nucleotides.

The labeling on the sugar is often used in the case of nucleic probes prepared by chemical synthesis.

Labeling on the phosphate has also been used for introducing functionalized arms and labels during chemical synthesis of oligonucleotides.

In fact, those skilled in the art who must perform a labeling of a nucleotide, or of a nucleotide analog or of a polynucleotide, are inclined to carry out this attachment on the base or on the sugar, which offer them greater convenience and more alternatives. This is, moreover, what emerges from the study of many documents, such as EP-A-0,329,198, EP-A-0,302,175, EP-A-0,097,373, EP-A-0,063,879, U.S. Pat. No. 5,449,767, U.S. Pat. No. 5,328,824, WO-A-93/16094, DE-A-3,910,151, EP-A-0,567,841 for the base or EP-A-0,286,898 for the sugar.

Binding of the label to the phosphate is a more complex technique than the technique consisting in functionalizing the base or the sugar, and has been less widely used, in particular because of the low reactivity of the phosphate (see, for example, Jencks W. P. et al J. Amer. Chem Soc., 82, 1778-1785, 1960). Similarly, in the review by O'Donnel and McLaughlin ("Reporter groups for the analysis of nucleic acid structure", p 216-243, in "Bioorganic Chemistry: Nucleic Acids", Ed Hecht S. M., Oxford University Press, 1996) relating to methods of introducing probes into oligonucleotide fragments, effective alkylation of the internucleotide phosphodiester is considered to be impossible.

The applicant has already developed a labeling technique based on novel reagents which are effective from the point of view of labeling yield, which are specific in terms of the labeling position, and in particular which do not affect the hybridization properties of the bases involved in the formation of the double helix, by means of hydrogen bonds, which can be used both for DNA and for RNA, and, finally, which make it possible to label without distinction natural polynucleotides or polynucleotides prepared by enzymatic amplification.

Thus, patent application WO-A-02/090319 describes many labels which satisfy the abovementioned conditions and which use the diazomethyl function as reactive function for the labeling. The diazomethyl function (of formula —C(N$_2$)—) has already been used for the alkylation of the phosphate groups, a certain number of problems arise. Firstly, diazo derivatives, in general, are themselves unstable, thereby posing problems for the use of these labeling reagents in a labeling kit, and, secondly, the coupling product is unstable, which is completely unacceptable if the function of the labeled product is to reveal the presence of a biological target molecule in any sample. Finally, derivatives bearing the diazomethyl function are water-insoluble, which results in the use of the two-phase conditions for the coupling with biological molecules, which are soluble and stable only in water or aqueous buffers, but these conditions slow down the reaction rate and are therefore detrimental to the coupling efficiency. The novel labeling reagents of this invention, described in application WO-A-02/090319, also solve these technical problems. According to one embodiment, the temperature-stable labeling reagent has the formula:

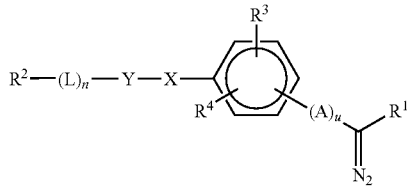

in which:
  $R^1$ represents H or an alkyl, aryl or substituted aryl group,
  $R^2$ represents a detectable label or at least two detectable labels connected to one another by at least one multimeric structure,
  L is a linker arm comprising a linear series of at least two covalent bonds and n is an integer equal to 0 or 1,
  $R^3$ and $R^4$ represent, independently of one another: H, NO$_2$, Cl, Br, F, I, $R^2$-(L)$_n$-Y—X—, OR, SR, NR$_2$, R, NHCOR, CONHR, COOR with R=alkyl or aryl,
  A is a linker arm comprising at least one covalent double bond allowing the conjugation of the diazo function with the aromatic ring and u is an integer between 0 and 2, preferably of 0 or 1, and
  —Y—X— represents —CONH—, —NHCO—, —CH$_2$O—, —CH$_2$S—.

In a further patent application filed by the applicant under number FR04/50600, dated Mar. 26, 2004, and entitled: "Labeling reagents, methods for synthesizing such reagents and methods for detecting biological molecules", these diazo-functional-based molecules were further improved, are still temperature-stable, and have the formula:

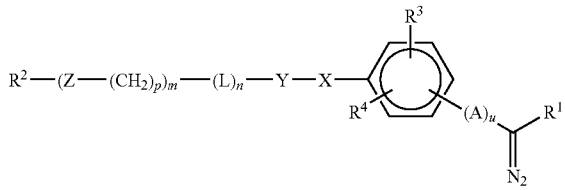

in which:
R¹ represents H or an alkyl, aryl or substituted aryl group,
R² represents a detectable label or at least two detectable labels connected to one another by at least one multimeric structure,
L is a linker arm comprising a linear series of at least two double bonds and n is an integer equal to 0 or 1,
R³ and R⁴ represent independently of one another: H, $NO_2$, Cl, Br, F, I, $R^2$-$(L)_n$-Y—X—, OR, SR, $NR_2$, R, NHCOR, CONHR, COOR, —CO—NH—$(CH_2)_3$—(O—$CH_2$—$CH_2)_3$—$CH_2$—NH—$R^2$, —CO—NH—$(CH_2)_3$—(O—$CH_2$—$CH_2)_4$—$CH_2$—NH—$R^2$ with R=alkyl or aryl,
A is a linker arm comprising at least one covalent double bond allowing the conjugation of the diazo function with the aromatic ring and u is an integer between 0 and 2, preferably of 0 or 1,
—Y—X— represents —CONH—, —NHCO—, —$CH_2$O—, —$CH_2$S—,
—Z— represents —NH—, —NHCO—, —CONH— or —O—,
m is an integer between 1 and 10, preferably between 1 and 3, and
p is an integer between 1 and 10, preferably between 1 and 3.

Furthermore, in order for this labeling to be even more effective, it is also advantageous for the natural or synthetic polynucleotides to also be fragmented. The reduced size of these nucleic acids makes them more accessible to the labeling. As regards the nucleic acid fragmentation, many methods are described in the prior art. Firstly, the fragmentation may be enzymatic, i.e. the nucleic acid fragmentation can be carried out with nucleases (DNases or RNases). Small fragments with 3'-OH, 5'-OH, 3'-phosphate or 5'-phosphate ends are then generated.

Secondly, the fragmentation may be chemical. For example, in the case of DNAs, depurination or depyrimidination may be carried out on said DNAs which are then fragmented in the presence of a base by means of a mechanism referred to as "beta-elimination". The DNA fragmentation can be carried out by means of mechanisms of oxidation, of alkylation, of addition of free radicals, inter alia.

In order to fragment RNAs or DNAs, as is described respectively in our U.S. Pat. No. 6,376,179 and patent application WO-A-01/44507, metal cations are used, often associated with organic molecules used as chemical catalysts, for example imidazole. This fragmentation is preferably carried out in an alkaline medium and generates fragments with 3'-phosphate ends. In this case, the binding of a label takes place at the only phosphate, of a nucleic acid fragment, that has been released during the cleavage. There is no specificity, it being possible for the fragmentation to be carried out on any type of nucleic acid and randomly. In fact, our method makes it possible, for example, to prepare a detection probe. Finally, the phosphate is merely a linker arm between the nucleic acid and the label.

The term "detectable label" is intended to mean at least one label capable of directly or indirectly generating a detectable signal. A nonlimiting list of these labels follows:
enzymes which produce a detectable signal, for example, by colorimetry, fluorescence or luminescence, such as horseradish peroxidase, alkaline phosphate, β-galactosidase or glucose-6-phosphate dehydrogenase,
chromophores, such as fluorescent, luminescent or dye compounds,
electron-dense groups that can be detected by electron microscopy or by their electrical property such as conductivity, amperometry, voltammetry or impedance,
detectable groups, for example the molecules of which are of sufficient sizes to induce detectable modifications of their physical and/or chemical characteristics; this detection can be carried out by optical methods such as diffraction, surface plasmon resonance, surface variation or contact angle variation, or physical methods such as atomic force spectroscopy or the tunnel effect,
radioactive molecules such as $^{32}P$, $^{35}S$ or $^{125}I$.

Preferably, the label is not a radioactive label so as to avoid problems of safety related to these labels.

For example, the label may be a fluorescent compound of low steric hindrance, such as fluorescein, dansyl, chromophores of the IR type (Li—COR Inc, Lincoln Nebr., USA), cyanine derivatives such as Cy5 and Cy3 (Randolph J. B. et al, Nucleic Acids Res., 25(14), p 2923-2929, 1997), and in particular Cy5 derivatives, or else the tracer is a hapten with low steric hindrance, such as biotin or an abietane derivative (see application WO-A-00/07982). The term "low steric hindrance" is intended to mean a molecular weight less than 2000 g/mol (for example, bis-bioPDAM having a weight of 1064 g/mol). In the case of a fluorophore, it is preferable to work with fluorophores for which the excitation wavelength is greater than 450 nm, preferably greater than 600 nm.

When the tracer is a hapten which does not produce a signal by itself, for instance biotin, the detection is carried out via the recognition of an anti-ligand labeled as described above. In the case of biotin, streptavidin or an anti-biotin antibody coupled to a fluorescent compound, such as fluorescein, Cy5 or phycoerythrin, is used. In the case of abietane, a monoclonal antibody as described in patent application WO-A-00/07982 is used.

This is what is referred to as labeling precursors. The term "labeling precursor" is intended to mean a compound having at least one optionally protected reactive function other than the diazomethyl function and compatible with said function, which allows the subsequent attachment of a label, i.e. after any of the steps of the method, and in particular after the oxidation step with $MnO_2$. In particular, the labeling precursor can comprise the linker arm L, described in the chemical formulae above. An example of the strategy using a label precursor is often associated with the case of signal amplification, but other variants are possible by using the various protective groups that are well known to those skilled in the art.

Indirect systems can also be used, for instance ligands capable of reacting with an antiligand.

Ligand/antiligand couples are well known to those skilled in the art, as is the case, for example, of the following couples:
biotin/streptavidin,
hapten/antibody,
antigen/antibody,
peptide/antibody,
sugar/lectin,
polynucleotide/sequence complementary to the polynucleotide.

In this case, it is the ligand which carries the linking agent. The antiligand may be detectable directly by means of the labels described in the previous paragraph, or by itself be detectable by means of a ligand/antiligand.

These indirect detection systems can result, under certain conditions, in a signal amplification, for example by using a multimeric structure. This signal amplification technique is well known to those skilled in the art, and reference may be made to the applicant's prior patent applications FR98/10084 or WO-A-95/08000 or to the article J. Histochem. Cytochem. 45: 481-491, 1997.

The term "multimeric structure" is intended to mean a polymer made up of repeat units of chemical or biological synthons. Many variants of such structures that can be used in the present invention are known, for instance:
- linear polymers (EP-A-0,561,722, EP-A-0,669,991),
- branched polymers (WO-A-01/92361),
- particles (EP-A-0 827 552),
- dendrimers (U.S. Pat. No. 4,507,466; U.S. Pat. No. 4,568,737; U.S. Pat. No. 6,083,708),
- polynucleotides, and
- polypeptides.

Another example of indirect systems uses a specific covalent bond between the ligand and the antiligand, for example methyl ketone and alkoxy amine. Examples of this system are described in patent applications WO-A-00/40590 and WO-A-98/05766. These indirect detection systems can result, under certain conditions, in signal amplification and reference may be made to the prior patent applications WO-A-00/07982, WO-A-01/92361 and WO-A-95/08000 for examples of chemical amplification using polymers, or to application WO-A-01/44506 for systems of chemical amplification by stacking.

In a specific implementation of the signal amplification, at least two labels are present on the labeling reagent.

In addition, the labeling reagents of the invention are soluble in polar and water-miscible solvents such as DMF, DMSO, $CH_3CN$, THF, DMA (dimethylacetamide), NMP (N-methyl-pyrrolidone) or DME (dimethoxyethane).

Preferably, the labeling reagents are soluble in DMSO or water.

The term "water-miscible solvent" is intended to mean a solvent which is miscible in a proportion of at least 5% by volume with water or an aqueous buffer containing salts.

The term "biological molecule" is intended to mean a compound which has at least one recognition site that allows it to react with a target molecule of biological interest. By way of example, mention may be made, as biological molecules, of nucleic acids, antigens, antibodies, polypeptides, proteins and haptens.

The term "nucleic acid" signifies a series of at least two deoxyribonucleotides or ribonucleotides, optionally comprising at least one modified nucleotide, for example at least one nucleotide comprising a modified base, such as inosine, methyl-5-deoxycytidine, dimethylamino-5-deoxyuridine, deoxyuridine, diamino-2,6-purine, bromo-5-deoxyuridine or any other modified base which allows hybridization. This polynucleotide can also be modified at the level of the internucleotide bond, for instance phosphorothioates, H-phosphonates or alkyl phosphonates, or at the level of the backbone, for instance alpha-oligonucleotides (FR-A-2 607 507) or PNAs (M. Egholm et al., J. Am. Chem. Soc., 114, 1895-1897, 1992 or 2'-O-alkyl ribonucleotides. The nucleic acid may be natural or synthetic, an oligonucleotide, a polynucleotide, a nucleic acid fragment, a ribosomal RNA, a messenger RNA, a transfer RNA, or a nucleic acid obtained by an enzymatic amplification technique such as:
- PCR (Polymerase Chain Reaction), described in U.S. Pat. No. 4,683,195, U.S. Pat. No. 4,683,202 and U.S. Pat. No. 4,800,159, and its derivative, RT-PCR (Reverse Transcription PCR), in particular in a one-step format, as described in patent EP-B-0,569,272,
- LCR (Ligase Chain Reaction), disclosed, for example, in patent application EP-A-0,201,184,
- RCR (Repair Chain Reaction), described in patent application WO-A-90/01069,
- 3SR (Self Sustained Sequence Replication) with patent application WO-A-90/06995,
- NASBA (Nucleic Acid Sequence-Based Amplification) with patent application WO-A-91/02818, and
- TMA (Transcription Mediated Amplification) with U.S. Pat. No. 5,399,491.

The term amplicons is then used to denote the nucleic acids generated by an enzymatic amplification technique.

Each of these modifications can be taken in combination provided that at least one phosphate is present in the nucleic acid.

The term "hapten" denotes nonimmunogenic compounds, i.e. incapable by themselves of promoting an immune reaction through antibody production, but capable of being recognized by antibodies obtained by immunizing animals under known conditions, in particular by immunization with a hapten-protein conjugate. These compounds generally have a molecular mass of less than 3000 Da, and most commonly less than 2000 Da, and can, for example, be glycosylated peptides, metabolites, vitamins, hormones, prostaglandins, toxins or various medicaments, nucleosides and nucleotides.

The term "purification step" is intended in particular to mean the separation between the nucleic acids of the microorganisms and the cellular constituents released in the lysis step which precedes the nucleic acid purification. These lysis steps are well known and, by way of indicative example, use may be made of the lysis methods as described in patent applications:
- WO-A-00/60049 regarding lysis by sonication,
- WO-A-00/05338 regarding magnetic and mechanical mixed lysis,
- WO-A-99/53304 regarding electrical lysis, and
- WO-A-99/15621 regarding mechanical lysis.

Those skilled in the art may use other well-known lysis methods, such as thermal or osmotic shocks or treatments with chaotropic agents, such as guanidium salts, in particular described in U.S. Pat. No. 5,234,809, belonging to the applicant.

This step generally makes it possible to concentrate the nucleic acids. By way of example, it is possible to use magnetic particles (in this respect, see the applicant's patents: U.S. Pat. No. 4,672,040 and U.S. Pat. No. 5,750,338), and thus to purify the nucleic acids, which are attached to these magnetic particles, by means of a washing step. This nucleic acid purification step is particularly advantageous if it is desired to subsequently amplify said nucleic acids. A particularly advantageous embodiment of these magnetic particles is described in patent applications WO-A-97/45202 and WO-A-99/35500.

The term "solid support" as used here, includes all the materials to which can be attached molecules carrying the diazomethyl function or a function derived therefrom, such as products of degradation or of rearrangement of the diazo, azines for example, released during the labeling reaction and which need to be eliminated. Synthetic materials or natural materials, which has optionally been chemically modified, can be used as solid support:
- in particular, polysaccharides, such as cellulose-based materials, for example paper, cellulose derivatives such as cellulose acetate and nitrocellulose, or dextran,
- in particular based on monomers of styrene type, natural fibers such as cotton, and synthetic fibers such as nylon; inorganic materials such as silica, quartz, glasses, ceramics; latices; magnetic particles; metal derivatives, gels, etc. The solid support can be in the form of a microtitration plate, a membrane, a particle or a substantially planar plate of glass or silicon or derivatives. These supports can also be functionalized with anionic and/or acid groups of interest, as will be subsequently explained, that can react with the diazo function or functions derived therefrom.

As mentioned above, the prior art also describes the use of compounds carrying diazo functions for the purpose of labeling nucleic acids, by bonding to their phosphate groups, for the purpose of making them detectable, in particular by fluorescence reading. In this case, the diazo compound carries a fluorescent group (fluorescein, Cy5) or a group (of the biotin, hapten or reactive function type) which allows covalent or noncovalent bonding with a fluorescent molecule.

The prior art describes the use of numerous means of purification associated with the labeling processes. Among these means, mention may be made of extraction with an organic phase, filtration and gel filtration. However, the reference technique is the use of silica, in powder form, of gel or of magnetic particles, for purifying the nucleic acids before or after labeling, in a process which results in detection by specific hybridization (concerning DNA chips, but also ELOSA plates or rapid test forms). The purification before labeling makes it possible to considerably improve the labeling yield, the post-labeling purification makes it possible to improve, in a determining manner, the hybridization yield and therefore the signal/noise ratio, necessary for good sensitivity of the test. In fact, the excess label used during the labeling and which has not reacted can considerably affect the hybridization.

Purification on silica necessitates a step for washing and for elution of the solid phase. The presence of three steps (attachment/washing/elution) therefore necessitates transfers of liquids, which are potentially factors of contamination and for material loss and, in general, moderately automatable. Furthermore, this process necessitates the intervention of a handler throughout the procedure, and the use of chaotropic (irritant) salts.

To summarize, the essential problem with all these labeling methods which have a purification step lies in the fact that, in order for the labeling to be really effective, it is necessary to use an excess of labels so that all the nucleic acids have the possibility of being labeled. The presence, in the treated liquid solution, of labeled nucleic acids but also of labels which have not reacted means that the liquid sample cannot subsequently be used in a specific detection step. It is necessary to remove the labels present in excess, beforehand. To do this, it is possible to bind the nucleic acids to particles of silica, optionally containing a magnetic material, in order to immobilize the labeled or unlabeled nucleic acids, and to wash them through elimination of the unwanted constituents. The applicant's U.S. Pat. No. 5,234,809, already mentioned above, allows this type of process. However, this generates additional steps which are costly in terms of time spent by practitioners and of the material.

The present invention therefore consists in using the chemical characteristics of a label or of a labeling precursor in order to allow its binding preferentially to a nucleic acid of interest and optionally, if such a binding has not occurred, to allow the capture thereof on a solid phase which does not lead to any washing phase. Furthermore, irritant chaotropic agents are not necessary for the purification process. Likewise, the method according to the invention does not require any additional system of pump or centrifuge type, intended to pass the liquid through the solid phase. The process may require a magnetization or filtration system, if the purification phase is composed of particles (magnetic or nonmagnetic); however, this device is not obligatory and a completely passive process (passage of the labeling medium over the solid phase) may be used. Finally, the method can be readily automated due to the use of solid phases and to its simplicity (bringing into contact, incubation, passage to hybridization). The method can be used in a system that uses a continuous flow, making it possible to simplify the integration into an autonomous device, "Lab-on-Card" type, or which is completely integrated in a single tube, of the purification of the nucleic acid with hybridization on a chip. This implies that the risks of contamination will be reduced and that there will be a decrease in the number of consumables used.

To this effect, according to a first embodiment, the present invention relates to a method for labeling biological molecules of interest contained in a biological sample, consisting in:
  a) providing a reaction vessel,
  b) immobilizing capture molecules, which are capable of binding a label or labeling precursor of the biological molecules of interest, on all or part of the inside surface of the vessel or of a solid support introduced into this vessel,
  c) introducing the biological sample into said reaction vessel, but also:
    1) at least one label or labeling precursor of the biological molecules of interest, and
    2) optionally, any ingredient required for labeling or prelabeling the biological molecules of interest,
  d) incubating the content of the reaction vessel,
  e) immobilizing the label or labeling precursor which is not reacted with the biological molecules of interest by binding to the capture molecules, and
  f) using the labeled biological molecules of interest, i.e. those which are reacted with said label or labeling precursor, for subsequent steps.

According to a second embodiment, the invention also relates to a method for treating a biological sample containing a mixture of biological molecules of interest and of at least one label or labeling precursor of the biological molecules of interest, optionally combined with any ingredient required for labeling the biological molecules of interest, consisting in:
  a) providing a reaction vessel,
  b) immobilizing capture molecules, which are capable of binding the label or labeling precursor of the biological molecules of interest, on all or part of the inside surface of the vessel or of a solid support introduced into this vessel,
  c) introducing the biological sample into said reaction vessel,
  d) incubating the content of the reaction vessel,
  e) immobilizing the label or labeling precursor which is not reacted with the biological molecules of interest by binding to the capture molecules, and
  f) using the labeled biological molecules of interest, i.e. those which are reacted with said label or labeling precursor, for subsequent steps.

In the two situations described above, and according to a preferential embodiment, the binding of the label or labeling precursor, which is not reacted with the biological molecules of interest, to the capture molecules takes place by means of a covalent bond.

In a specific embodiment, and prior to step a) described above, the biological sample is treated according to at least one of the following steps:
  transfer from another reaction vessel upstream,
  lysis of a complex biological material in order to make the biological molecules of interest accessible and/or detectable,
  capture or isolation of the biological molecules of interest, and/or treatment of the biological molecules of interest in order to make their detection possible or to enhance their detection; this treatment can consist, for example, of a thermal treatment.

In another specific embodiment, step f) described above is followed by at least one subsequent step below:
- transfer to another reaction vessel downstream,
- labeling of the prelabeled biological molecules of interest,
- purification of the labeled or prelabeled biological molecules of interest, and/or
- detection of the labeled biological molecules of interest hybridized to capture probes.

The detection of the biological molecules of interest can, for example, be carried out advantageously in a homogeneous phase, with or without hybridization with a detection molecule (for example, a nucleic probe).

In all the above situations, it is possible for the inside surface of the vessel or the solid support introduced into this vessel to carry anionic and/or acid functions, and for the label or labeling precursor to comprise a diazo function (—N=N).

In the latter embodiment, the functions carried by the inside surface of the vessel or the solid support introduced into this vessel consist of carboxylic and/or sulfonic functions.

In all these situations, the biological molecules of interest consist of nucleic acids and/or nucleic acid fragments.

In the latter embodiment, the nucleic acids and/or the nucleic acid fragments consist of DNA, RNA, DNA-RNA chimeric polymers, which may optionally contain at least one nucleotide thiophosphate, an LNA, a 2'-O-Me and/or a methylphosphonate derivative.

In the embodiments where the biological molecules of interest are nucleic acids or nucleic acid fragments, prior to step a) defined above, the biological sample is treated according to at least one of the following steps:
- transfer from another reaction vessel upstream,
- lysis of the complex biological material, contained by the biological sample, in order to make the nucleic acids accessible,
- extraction of the nucleic acids from the complex biological material,
- specific amplification of the nucleic acids of interest,
- fragmentation of said nucleic acids of interest or amplicons, and/or
- transcription or reverse transcription of a nucleic acid of interest, without any notable amplification phenomenon.

Still in the same situation, step f) defined above is followed by at least one subsequent step below:
- transfer to another reaction vessel downstream,
- labeling of the prelabeled nucleic acids,
- purification of the labeled or prelabeled nucleic acids,
- detection of the labeled or prelabeled nucleic acids hybridized to capture probes,
- transcription or reverse transcription of a nucleic acid of interest, without any notable amplification phenomenon, and/or
- homogeneous-phase detection of the labeled or prelabeled nucleic acids, with or without the use of detection probes.

According to another embodiment of the invention, the capture molecules are present in excess relative to the labels, and the labels are present in excess relative to the biological molecules of interest which will be labeled.

More particularly, the capture molecules are present in excess relative to the free labels which do not react with the nucleic acids, and the labels are present in excess relative to the nucleic acids which will be labeled.

In order to allow the detection and/or quantification and/or purification of the nucleic acid of interest, the labeled nucleic acid is capable of forming a complex sufficiently complementary to the target to hybridize specifically according to the reaction conditions, and in particular the conditions of temperature or of salinity of the reaction medium.

Furthermore, the labels which have not reacted or free labels conserve their reactive function intact and are therefore capable of subsequently reacting with the capture molecules, which themselves carry a complementary reactive function, without, however, this reaction being specific. The reactive function and the complementary reactive function therefore form a covalent bond, thereby allowing the immobilization of the free labels, the biological sample then containing only labels associated with nucleic acids.

The attached figures show the various steps of the method of purification according to the invention. They represent a specific embodiment and cannot be considered to limit the scope of the present invention.

FIG. 1 represents a view in transverse section of a reaction vessel in which the method of purification is carried out. This vessel comprises an upper lid and a lower body hollowed out so as to create a space where the method according to the invention can be carried out. This space comprises a supply channel on the left which allows the biological sample to be treated to enter, and a discharge channel on the right which allows said treated biological sample to exit. The inside space of the vessel is treated or is coated so as to exhibit capture molecules carrying carboxylic reactive functions. The inside space of the lid could also undergo the treatment.

As mentioned above, the supply channel allows the introduction, in the direction of the arrow, of a liquid biological sample containing, inter alia, nucleic acids and labels, carrying a diazo function. In the case represented in this figure, the nucleic acids are not yet labeled, but it is also possible for them to be put into contact with the labels beforehand.

FIG. 2 represents a view identical to FIG. 1, in which the biological sample present in the inside space of the reaction vessel contains labeled nucleic acids and free labels, i.e. labels which have not reacted with the nucleic acids. Due to the fact that the labels are present in excess relative to the nucleic acids, all these nucleic acids will be labeled, the other side of this being that there are numerous free labels.

FIG. 3 is still identical to FIGS. 1 and 2, but it is noted that, after a certain period of time, i.e., in general, in the case of bis-BioPDAM, of at least ten or so minutes but less than one hour, the free labels are predominantly bound to the carboxylic reactive functions present in the inside space of the vessel. The term "predominantly" is intended to mean that the free labels are captured so that they are below the inhibitory concentration (less than 2 mM). It is quite obvious that these reactive functions are present in excess relative to the free labels which have not reacted with the nucleic acids.

Figure 6:
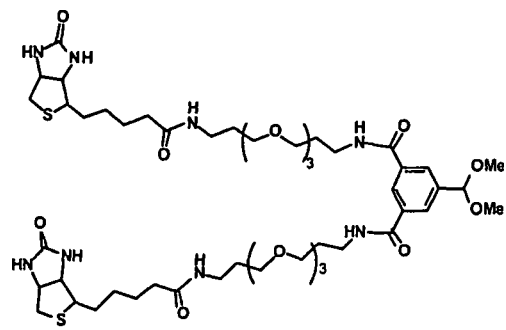

Finally, FIG. 6 represents the structural formula of the N,N'-bis(13-biotinoylamino-4,7,10-trioxatridecyl)-5-

(dimethoxy methyl)isophthalamide molecule, also subsequently referred to as "acetal" in order to facilitate understanding of the text.

EXAMPLE 1

Labeling and Purification on Carboxylic Particles of the RT-PCR Amplification Product Followed by Analysis on a DNA Chip (Affymetrix, Santa Clara, Calif.)

In the present example, the binding of the free labels does not take place directly on a solid support, but it makes it possible to control the validity of the concept of the invention by testing the reactivity of the labels with magnetic particles.
A—Influenza B PCR:

This experiment is carried out on an "Influenza B" model.

This name denotes the amplicons generated by RT-PCR from a sequence of 190 bases of a fragment of the Influenza B virus RNA gene.

The conditions for the preparation of the samples, the viral RNA extraction, the amplification of said viral RNAs and the sequence of the primers are described in the article "Effectiveness of Reverse Transcription-PCR, Virus Isolation, and Enzyme-linked Immunosorbent Assay for diagnosis of Influenza A Virus Infection in different Age Groups", Steininger C. et al., *J. Clin. Microbiol.*, (2002); 40(6), 2051-2056.

The RT-PCR is carried out using preparations of viral RNA ($10^3$ copies per amplification) as starting template, with the Titan One Tube RT-PCR System kit (Roche Diagnostic Corporation, Basle, Switzerland, reference: 11 855 476 001) with 0.2 mM of each deoxyribonucleotide, 0.3 µM of primers and 0.4 µl of enzyme.

The parameters of the RT-PCR cycle are the following: 60° C. for 30 minutes in order to carry out the Reverse Transcription reaction, 40 cycles according to the following protocol: 94° C. for 20 seconds, then 50° C. for 30 seconds and, finally, 72° C. for 30 seconds, then 4° C. until the thermocycler has stopped.

The amplicons derived from the RT-PCR described above are subsequently referred to by the terms "PCR Influenza B".
B—Homogeneous-Phase Labeling (Reference Protocol):

Homogeneous-phase labeling is used as reference or "control" technique relative to the invention.

The protocol was developed using a final concentration of label (2 mM) sufficient to allow sufficient labeling of the DNA, but less than the threshold above which the free label affects the hybridization.

Figure 1:
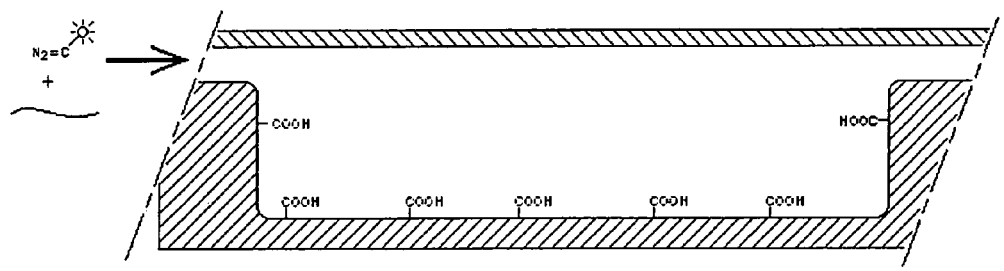
Figure 2:
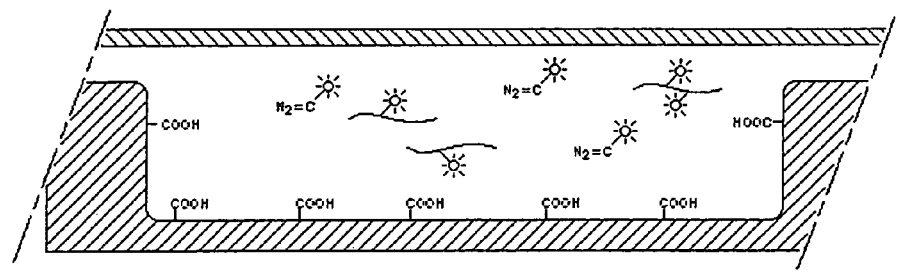
Figure 3:
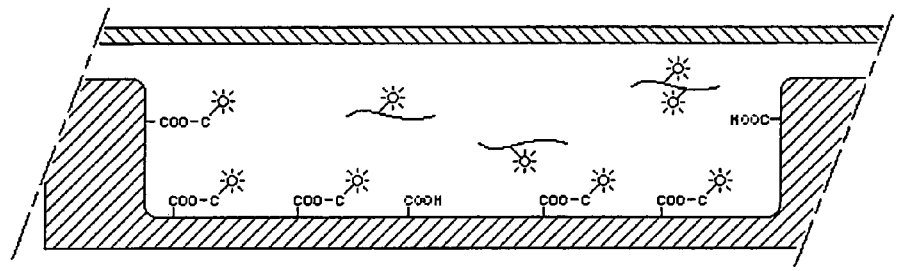
Figure 4:
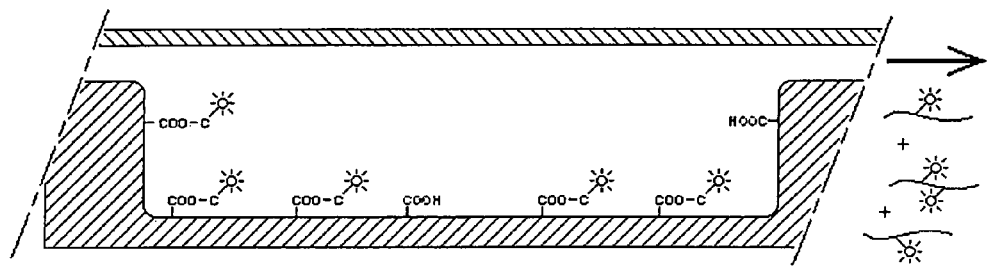
FIG. 4 is still identical to FIGS. 1 to 3. As mentioned above, the exit channel allows the treated liquid biological sample, containing, inter alia, labeled nucleic acids but no free labels, to exit in the direction of the arrow on the right of the figure.
Figure 5:
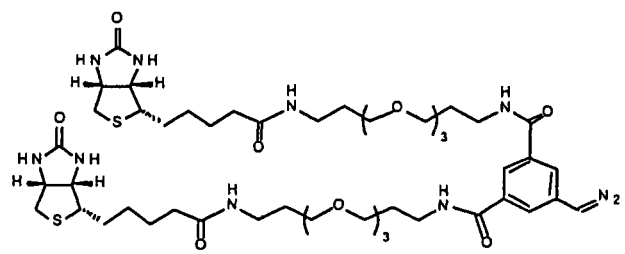
FIG. 5 represents the structural formula of the N,N'-bis(13-biotinoylamino-4,7,10-trioxatridecyl)-5-(diazomethyl) isophthal amide molecule, also subsequently referred to as "bis-BioPDAM" in order to facilitate understanding of the text.

A volume of 5 µl of PCR Influenza B, is mixed with 5 µl of compound N,N'-bis(13-biotinoylamino-4,7,10-trioxatridecyl)-5-(diazomethyl)isophthalamide, hereinafter referred to as "bis-BioPDAM", see FIG. 5, diluted to 6 mM in dimethyl sulfoxide, hereinafter referred to as "DMSO", and 5 µl of $H_2O$, and then incubated for 10 minutes at 80° C.

The reaction medium is subsequently brought into contact with the DNA chip (Affymetrix, Santa Clara, Calif.) for the hybridization step using the supplier's protocol. The DNA chip used is designed for the analysis of the region amplified during the RT-PCR. A description of the hybridization protocol and also a description of the technologies used for the analysis of the results are described by A. Troesch et al.: "Mycobacterium species identification and rifampin resistance testing with high-density DNA probe arrays" *J. Clin. Microbiol.* (1999), 37, 49-55.

The reading of the fluorescence emitted at the surface of the DNA chip after labeling and hybridization, and also the generation of the data in terms of signal intensity and percentage homology, are carried out by means of the reading systems and the software provided by the Genechip® Instrument system and Genechip Information System® (Affymetrix, Santa Clara, Calif.).

The reading system provides signal and background noise intensities expressed in RFU ("Relative Fluorecent Units"). The percentage homology is given relative to a reference sequence (corresponding to the amplified target sequence, obtained by sequencing).

The results in terms of median intensity of the signal (I), of background noise (B) and of percentage homology (% homology) are given in a results table.

In general, it is considered that a percentage homology above 90% is a satisfactory result, although a result above 95% is generally sought. A high intensity with a low background noise (high I/B ratio) is the second result sought in the set-ups.
C—Homogeneous-Phase Labeling at Inhibitory Label Concentration (Control):

In this experiment, a higher final concentration of the bis-BioPDAM label is used (5 mM). This concentration affects the hybridization in the absence of purification, but makes it possible to obtain a greater signal (due to a higher labeling yield) when this same reaction medium is effectively purified.

A volume of 5 µl of PCR Influenza B is mixed with 5 µl of bis-BioPDAM, diluted to 15 mM in DMSO, and 5 µl of $H_2O$, and then incubated for 10 minutes at 80° C.

The reaction medium is subsequently brought into contact with the chip for hybridization and detection according to the protocol described in paragraph B above.
D—Homogeneous-Phase Labeling with Silica-Membrane Purification (Control):

In this experiment, nucleic acid purification columns containing a silica membrane, sold by QIAgen GmbH (Hilden, Germany) were used. This technique constitutes the reference method. In this case, the labeling protocol was carried out using a higher final concentration of bis-BioPDAM (5 mM), which label concentration affects the on-chip hybridization in the absence of effective purification.

A volume of 5 µl of PCR Influenza B is mixed with 5 µl of bis-BioPDAM, diluted to 15 mM in DMSO, and 5 µl of $H_2O$, and then incubated for 10 minutes at 80° C.

The reaction medium is subsequently purified using the QIAQuick kit (QIAgen GmbH, Hilden, Germany. Reference: 28 306) using the protocol recommended by the supplier, and is then brought into contact with the DNA chip for the hybridization according to the protocol described in paragraph B already described.
E—Homogeneous-Phase Labeling with Purification on Carboxylic Particles (Invention):

In this experiment, a labeling product, obtained using a higher final concentration of bis-BioPDAM (5 mM) is purified with a carboxylic solid phase (invention). The 5 mM label concentration affects the hybridization in the absence of an effective purification step. This is therefore the concentration selected for studying the effectiveness of the purification.

A volume of 5 µl of PCR Influenza B is mixed with 5 µl of bis-BioPDAM, diluted to 15 mM in DMSO, and 5 µl of $H_2O$, and then incubated for 10 minutes at 80° C.

The reaction medium is subsequently incubated for 10 minutes at ambient temperature using 2.5 mg of Standard Carboxyl-Adembeads (reference: 0213, Ademtech, Pessac, France, hereinafter referred to as "carboxylic particles"), the particles are subsequently separated by magnetization of the reaction medium, and the latter is brought into contact with the DNA chip for the hybridization step according to the protocol described above in paragraph B.

F—Results and Conclusion:

The results in terms of percentage homology, signal intensity (I) and background noise (B) are given in table 1 below:

TABLE 1

Comparative study of the method using the invention compared with controls without purification or with purification on a silica membrane

| Labeling method | % Homology | I | B | I/B |
|---|---|---|---|---|
| B - Homogeneous-phase labeling (reference) | 93.1 | 1699 | 308 | 5.5 |
| C - Homogeneous-phase labeling at a label concentration (5 mM) which affects hybridization (control): | 47.5 | 135 | 339 | 0.3 |
| D - Homogeneous-phase labeling with silica-membrane purification (control): | 97.9 | 5905 | 297 | 19.9 |
| E - Homogeneous-phase labeling with purification on carboxylic particles (invention) | 97.9 | 8167 | 434 | 18.7 |

The results are expressed as percentage homology, as signal intensity (I) and as background noise (B).

In conclusion, the results obtained with the reference method are substantially identical to those obtained with the silica-membrane purification. Furthermore, it is observed that the results obtained using the "carboxylic purification" are better, in terms of intensity (I), than those obtained without purification, or using a silica-membrane purification. An increase in the signal on the chip makes it possible to have a more sound test, less dependent on factors that locally impact on the background noise (dust, precipitates appearing on the chip, for example). Furthermore, the ease with which the purification protocol can be carried out considerably lightens the handling process.

EXAMPLE 2

Labeling And Purification on Carboxylic Particles of the Labeled RT-PCR Amplification Product Contaminated with a Nonreactional Equivalent of the Label This example serves to demonstrate that the bond that is created between the solid support and the labeling molecule is indeed the result of a covalent capture of the label and not of its adsorption onto said support.

A—Objective:

In this experiment, a purified labeling product is contaminated with a synthesis intermediate of the bis-BioPDAM, N,N'-bis(13-biotinoylamino-4,7,10-trioxatridecyl)-5-(dimethoxy methyl)isophthalamide, hereinafter referred to as "acetal", FIG. 6. This reactant does not carry the diazomethyl function, and cannot therefore react with the carboxylic functions.

On the other hand, it has the entire structure of bis-BioPDAM, and can therefore adsorb to the surfaces in a manner similar to bis-BioPDAM, when the purification phenomena observed are nonspecific adsorption phenomena, instead of phenomena involving specific bonds.

The acetal affects the nucleic acid hybridization in the same way as the bis-bioPDAM, thereby making it possible to judge the quality of the elimination thereof.

B—Experiment:

A volume of 5 µl of PCR Influenza B is mixed with 5 µl of bis-BioPDAM, diluted to 15 mM in DMSO, and 5 µl of $H_2O$, and then incubated for 10 minutes at 80° C. The reaction medium is subsequently purified using the QIAQuick kit (QIAgen GmbH, Hilden, Germany. Reference: 28 306) using the supplier's protocol.

This preparation is carried out in parallel on several aliquots of a sample having been subjected to an RT-PCR amplification, in order to have a volume of purified product sufficient to carry out several controls. The purification products are mixed in order to eliminate the variations induced by the preparation of said sample.

Fractions of 15 µl, corresponding to the volume of eluate obtained after purification by means of the silica-membrane purification of the mixture, are subsequently treated in the following way:

a) direct hybridization on an Affymetrix chip as described in example 1/B (reference).
b) addition of 5 mM of acetal hybridization on an Affymetrix chip as described in example 1/B (control for the inhibition by the acetal).
c) purification for 10 minutes at ambient temperature on carboxylic particles, as described in example 1/E, and then hybridization on an Affymetrix chip as described in example 1/B (control for the action of the particles on the labeling product).
d) addition of 5 mM of acetal and then purification for 10 minutes at ambient temperature on carboxylic particles, as described in example 1/E, and hybridization on an Affymetrix chip as described in example 1/B (control for the action of the particles on the acetal).

C—Results and Conclusion:

The results in terms of percentage homology, signal intensity (I) and background noise (B) are given in table 2 below:

TABLE 2

Comparative study of the method using the invention (C and D) compared with two controls (A and B) not using it, in the presence of an inhibitory compound which cannot react on the carboxylic function (B and D)

| Labeling method | % Homology | I | B | I/B |
|---|---|---|---|---|
| A - Reference | 93.1 | 1699 | 308 | 5.5 |
| B - Control for the inhibition by the acetal | 39.5 | 127 | 260 | 0.5 |
| C - Control for the action of the carboxylic particles on the label | 97.4 | 1911 | 302 | 6.3 |
| D - Control for the action of the carboxylic particles on the acetal | 50.0 | 525 | 369 | 1.4 |

The results are also expressed as percentage homology, as signal intensity (I) and as background noise (B).

In conclusion, the acetal derivative affects the hybridization of the nucleic acids (B and D), irrespective of whether or not there is a pretreatment with carboxylic particles (D). This result indicates that, in the absence of reaction with the carboxylic function, the acetal cannot react. There is therefore no notable elimination of the acetal compound by adsorption. It can therefore be concluded that the diazomethyl-carboxylic acid reaction which results in a covalent bond is the principal mechanism involved in the purification of the reaction medium.

EXAMPLE 3

Labeling and Carboxylic-Membrane Purification of the Labeled RT-PCR Amplification Product A—Objective:

In this experiment, a labeling product, obtained using a final concentration of bis-BioPDAM of 5 mM, is purified using a membrane carrying carboxylic functions (Biodyne C, reference S60314, Pall Gelman Sciences, New York, USA, hereinafter referred to as Biodyne C). The 5 mM label concentration affects the hybridization in the absence of an effective purification step. This is therefore the concentration selected for studying the effectiveness of the purification.

B—Experiment:

A volume of 5 µl of PCR Influenza B is mixed with 5 µl of bis-BioPDAM, diluted to 15 mM in DMSO, and 5 µl of H$_2$O, and then incubated for 10 minutes at 80° C. This experiment is carried out in duplicate, and the labeling products are then mixed and divided into two equal volumes in order to limit the potentially detrimental effects due to a variability in the protocol for the procedure. The reaction medium is subsequently incubated for 10 minutes at ambient temperature using 6 mM$^2$ of Biodyne C (b), or left at ambient temperature (reference a), and then this medium treated in this way is brought into contact with the DNA chip for the hybridization step according to the protocol described in example 1/B.

C—Results and Conclusion:

The results in terms of percentage homology, signal intensity (I) and background noise (B) are given in table 3 below:

TABLE 3

Comparative study of a method using the invention
(b) compared with a reference not using it (a)

| Labeling method | % Homology | I | B | I/B |
| --- | --- | --- | --- | --- |
| a Reference | 94.7 | 4252 | 564 | 7.5 |
| b - Carboxylic-membrane purification | 94.7 | 23811 | 2174 | 11.0 |

The results are once again expressed as percentage homology, as signal intensity (I) and as background noise (B).

In conclusion, the Biodyne C membrane, carrying carboxylic functions, makes it possible to obtain a purification of the sample that is the same as with magnetic particles.

EXAMPLE 4

Labeling and Purification with a Carboxylic Polymer of the Labeled RT-PCR Amplification Product A—Objective:

In this experiment, a labeling product obtained using a final concentration of bis-BioPDAM of 5 mM is purified using a polymer carrying carboxylic functions (Poly-Acrylic Acid sodium salt) standard 28'000, reference 81124, Fluka, Buchs, Switzerland; hereinafter referred to as APA). As described above, the 5 mM label concentration affects the hybridization in the absence of an effective purification step.

B—Myco 16 S PCR:

This experiment is carried out on a "Myco 16S" model, which denotes the amplicons generated by PCR from a 180 base sequence of a fragment of the gene encoding the 16S ribosomal RNA of *Mycobacterium tuberculosis.*

The conditions for the culturing, the extraction of the mycobacteria and also the amplification primers are given by A. Troesch et al.: "Mycobacterium species identification and rifampin resistance testing with high-density DNA probe arrays" *J. Clin. Microbiol.* (1999), 37, 49-55.

The PCR is carried out using preparations of genomic DNA (10$^3$ copies per PCR) as starting template, with the FastStart High Fidelity PCR System kit (Roche Diagnostic Corporation, Basle, Switzerland, reference: 03 553 426 001) with 0.2 mM of each deoxyribonucleotide, 0.3 µM of primers and 0.4 µl of enzyme.

The parameters of the PCR cycle are the following: 95° C. for 4 minutes and then 35 amplification cycles according to the following protocol: 95° C. for 30 seconds, then 55° C. for 30 seconds and, finally, 72° C. for 30 seconds. Finally, the mixture is maintained at 4° C. until the thermocycler is stopped, in order to prevent any possible degradation of the amplicons at ambient temperature.

The solution containing the PCR-derived amplicons, described above, is subsequently referred to as "PCR 16S".

C—Experiment:

A volume of 5 µl of PCR 16S is mixed with 5 µl of bis-BioPDAM, diluted to 2.5 mM in DMSO, and 15 µl of H$_2$O, and then incubated for 10 minutes at 80° C. This experiment is carried out in duplicate, and the labeling products are then mixed and divided into two equal volumes in order to limit the potentially detrimental effects due to a variability in the protocol for the procedure.

The reaction medium is subsequently incubated for 10 minutes at ambient temperature (a), or with a pellet of 10 µl of solution containing 20% of APA, dried under an air vacuum (b), and is then brought into contact with the DNA chip for the hybridization step according to the protocol described in example 1/B.

D—Results and Conclusion:

The results in terms of percentage homology, signal intensity (I) and background noise (B) are given in table 4 below:

TABLE 4

Comparative study of a method using the invention
(b) compared with a reference not using it (a)

| Labeling method | % Homology | I | B | I/B |
| --- | --- | --- | --- | --- |
| a - Reference | 97.9 | 2313 | 525 | 4.4 |
| b - Purification with APA | 94.4 | 8091 | 928 | 8.7 |

In conclusion, the polymer carrying carboxylic functions makes it possible to obtain purification of the sample which is comparable to that carried out using magnetic particles.

EXAMPLE 5

Labeling and Purification with a Sulfonic Polymer, of the Labeled RT-PCR Amplification Product Contaminated with a Nonreactional Equivalent of the Label A—Objective:

In this experiment, a labeling product, obtained using a final concentration of bis-BioPDAM of 5 mM, is purified using a polymer carrying sulfonic functions (reference 29 256-7, Sigma-Aldrich, Saint-Louis; Mich., USA, hereinafter referred to as Nafion).

B—Experiment:

A volume of 5 µl of PCR 16S is mixed with 5 µl of bis-BioPDAM, diluted to 2.5 mM in DMSO, and 15 µl of H$_2$O, and then incubated for 10 minutes at 80° C. This experiment is carried out in duplicate and then the labeling products are mixed and divided into two equal volumes in order to limit the potentially detrimental effects due to a variability in the protocol for the procedure.

The reaction medium is subsequently incubated:
for 10 minutes at ambient temperature (a) or
with a pellet of 10 µl of Nafion at 5% in methanol, dried under an air vacuum (b),
and is then brought into contact with the DNA chip for the hybridization step according to the protocol described in example 1/B.

C—Results and Conclusion:

The results in terms of percentage homology, signal intensity (I) and background noise (B) are given in table 5 below:

TABLE 5

Comparative study of a method using the invention
(b) compared with a reference not using it (a)

| Labeling method | % Homology | I | B | I/B |
|---|---|---|---|---|
| a - Reference | 97.9 | 2313 | 525 | 4.4 |
| b - Purification with Nafion | 97.2 | 8887 | 1002 | 8.9 |

The results are once again expressed as percentage homology, as signal intensity (I) and as background noise (B).

In conclusion, the polymer carrying the sulfonic functions makes it possible to obtain purification of the sample which is comparable to those obtained with magnetic particles.

GENERAL CONCLUSION

The method according to our invention is based on the use of the reactivity of the diazomethyl function with respect to acids (carboxylic function in particular) for the purpose of capturing the excess label after the labeling step. This reactivity is known to those skilled in the art. By way of example, mention may be made of the 4-(diazomethyl)phenoxymethyl-polystyrene (reference 17338, Fluka, Buchs, Switzerland) used for covalently bonding proteins via their carboxylic bonds. This resin was used by the applicant in the context of nucleic acid capture experiments. The idea of using the reactivity of diazomethyl functions with respect to a solid support in a post-labeling purification process is unknown at this time.

The reaction is based on the conservation of the reactivity of the diazo function after the labeling step. This conservation of the reactivity is not at all evident, since some of the functions could be hydrolyzed in the reaction medium during the initial labeling step. The fact that a not insignificant part of the labels which have not reacted with the nucleic acids is still reactive, and that the immobilization on a solid phase is carried out with a yield sufficient to allow hybridization of the sample, is a surprising result.

The high reactivity of the diazo function with the carboxylic function makes it possible to carry out the reaction at ambient temperature for a period of time limited to a few minutes. This approach based on a covalent bonding is an innovation compared with the equivalent techniques.

Since the label molecules are covalently sequestered on a solid support or on a soluble polymer, there is no need to wash after purification. The elimination of the washing step is an innovation compared with the existing purification methods.

Since the method which is the subject of the invention is based on a chemical reaction, it is more specific and selective than filtration, than phase-exclusion purification, or than adsorption onto a solid support. The risks of loss of the biological sample by adsorption are reduced.

Finally, the purification support can be readily integrated into a consumable, whether this is a tube in the case of a manual method, or a component of card type for an automated protocol.

What is claimed is:

1. A method for labeling nucleic acids, the method comprising:
   introducing the nucleic acids and labels or labeling precursors into a reaction chamber, the labels or labeling precursors comprising a diazo function and the reaction chamber having immobilized capture molecules capable of binding the labels or labeling precursors at least partially on an inner surface of, or on a solid support in, the reaction chamber;
   reacting the nucleic acids with the labels or labeling precursors to label or pre-label, respectively, the nucleic acids by reacting the diazo function with phosphate groups of the nucleic acids; and
   covalently bonding unreacted labels or labeling precursors to the capture molecules.

2. A method for treating a biological sample containing nucleic acids of interest, the method comprising:
   introducing the biological sample and labels or labeling precursors into a reaction chamber, the labels or labeling precursors comprising a diazo function and the reaction chamber having immobilized capture molecules capable of binding the labels or labeling precursors at least partially on an inner surface of, or on a solid support in, the reaction chamber;
   reacting the nucleic acids of interest with the labels or labeling precursors to label or pre-label, respectively, the nucleic acids by reacting the diazo function with phosphate groups of the nucleic acids; and
   covalently bonding unreacted labels or labeling precursors to the capture molecules.

3. The method as claimed in claim 2, wherein, prior to introducing the biological sample into the reaction chamber, the method further comprises at least one of the following steps:
   transferring the biological sample to the reaction chamber from an upstream reaction chamber,
   lysing a complex biological material in order to make the nucleic acids of interest accessible and/or detectable,
   capturing or isolating the nucleic acids of interest, and
   treating the nucleic acids of interest in order to make their detection possible or to enhance their detection.

4. The method as claimed in claim 2, wherein the method further comprises at least one subsequent step below:
   transferring the labeled or pre-labeled nucleic acids of interest to another reaction chamber downstream,
   labeling the pre-labeled nucleic acids of interest to obtain labeled nucleic acids,
   purifying the labeled or pre-labeled nucleic acids of interest, and
   detecting nucleic acids of interest that are hybridized to capture probes.

5. The method as claimed in claim 1, wherein the inside surface of, or the solid support in, the reaction chamber comprises carboxylic and/or sulfonic functions.

6. The method as claimed in claim 1, wherein the nucleic acids are selected from the group consisting of DNA, RNA, and DNA-RNA chimeric polymers, which optionally contain at least one nucleotide thiophosphate, an LNA, a 2'-O-Me and/or a methylphosphonate derivative.

7. The method as claimed in claim 3, wherein, prior to introducing the biological sample into the reaction chamber, the method further comprises treating the biological sample according to at least one of the following steps:
   extracting nucleic acids from the complex biological material, performing specific amplification of the nucleic acids of interest, fragmenting the nucleic acids of interest or amplicons, and transcribing or reverse transcribing the nucleic acids of interest, without amplification.

8. The method as claimed in claim 4, wherein the method further comprises at least one subsequent step below:

transcribing or reverse transcribing the nucleic acids of interest, without amplification and detecting by homogeneous-phase detection the labeled or pre-labeled nucleic acids, with or without the use of detection probes.

9. The method as claimed in claim 1, wherein the capture molecules are present in excess relative to the labels or labeling precursors, and the labels or labeling precursors are present in excess relative to the nucleic acids to be labeled or pre-labeled.

10. The method as claimed in claim 1, wherein the capture molecules are present in excess relative to the unreacted labels or labeling precursors, and the labels or labeling precursors are present in excess relative to the nucleic acids to be labeled or pre-labeled.

11. The method as claimed in claim 1, wherein the capture molecules comprise carboxylic and/or sulfonic functions, and the unreacted labels or labeling precursors are covalently bonded to the capture molecules by reacting the diazo function with the carboxylic and/or sulfonic functions.

12. The method as claimed in claim 2, wherein the capture molecules comprise carboxylic and/or sulfonic functions, and the unreacted labels or labeling precursors are covalently bonded to the capture molecules by reacting the diazo function with the carboxylic and/or sulfonic functions.

13. The method as claimed in claim 1, wherein the reaction chamber is a single reaction chamber in which the nucleic acids are reacted with the labels or labeling precursors and the unreacted labels or labeling precursors are covalently bonded to the capture molecules.

14. The method as claimed in claim 2, wherein the reaction chamber is a single reaction chamber in which the nucleic acids of interest are reacted with the labels or labeling precursors and the unreacted labels or labeling precursors are covalently bonded to the capture molecules.

\* \* \* \* \*